United States Patent [19]
Kreft et al.

[11] Patent Number: 5,776,967
[45] Date of Patent: Jul. 7, 1998

[54] PYRANOINDOLE INHIBITORS OF COX—2

[75] Inventors: Anthony F. Kreft, Langhorne, Pa.; Craig E. Caufield; Amedeo A. Failli, both of Princeton Junction, N.J.; Thomas J. Caggiano, Morrisville, Pa.; Alexander A. Greenfield, Princeton Junction, N.J.; Dennis M. Kubrak, Philadelphia, Pa.

[73] Assignee: American Home Products Corporation, Madison, N.J.

[21] Appl. No.: 888,983

[22] Filed: Jul. 7, 1997

[51] Int. Cl.$^6$ .......................... A61K 31/40; A61K 31/35; C07D 209/80; C07D 311/78
[52] U.S. Cl. .......................... 514/411; 514/454; 548/439; 549/385; 560/21; 560/56
[58] Field of Search .......................... 514/411, 454; 548/439; 549/385; 560/21, 56

[56] References Cited

U.S. PATENT DOCUMENTS 4,686,213  8/1987  Ferdinandi et al. .......... 514/161
4,927,842  5/1990  Mobilio .......................... 514/411

OTHER PUBLICATIONS

Humber et al., Etodolac, a Novel Antiinflammatory Agent. The Synthesis and Biological Evaluation of Its Metabolites, *J. Am. Chem. Coc*, 1988, 31:1712–1719.

Lewis and Kreft, A Review on the Strategies for the Development and Application of New Anti–arthritic Agents, Immunopharmacol.Immunotoxicol., 1995, 17:607–663.

Marcus, Aspirin as Prophalaxis Against Colorectal Cancer, New. Eng. J. Med., 1995, 333:656–657.

Vane et al., The mode of action of anti–inflammatroy drugs, Postgrad. Med. J., 1990, 66(Suppl 4):S2–S17.

Brooks et al., Nonsteroidal Antiinflammtory Drug–Differences and Similarities, 1991, New Eng. J. Med., 324:1716–1725.

Dajani et al., Prevention and Treatment of Ulcers Induced by Nonsteroidal Anti–Inflammatory Drugs: An Update, 1995, J. Physiol. Pharmacol., 46:3–16.

Somasundaram et al., The Biochemical Basis of Non–Steroidal Anti–Inflammatory Drug–Induced Damage to the Gastrointestinal Tract: A Review and a Hypothesis, 1995, Scand J. Gastroenterol, 30:289–299.

Hayllar et al., NSAIDs, Cox–2 inhibitors, and the gut, 1995, Lancet, 346:521–522.

O'Neill et al., Overexpression of Human Prostaglandin G/H Synthase–1 and –2 by Recombinant Vaccina Virus: Inhibition by Nonsteroidal Anti–inflammatory Drugs and Biosynthesis of 15–Hydroxyeicosatetraenoic Acid,1994,Molec. Pharmacol.,45:245–254.

Laneuville et al., Differential Inhibiton of Human Prostaglandin Endoperoxide H Synthases–1 and –2 by Nonsteroidal Ant–inflammatory Drugs, 1994, Pharmacol. Exp. Ther., 271:927–934.

Mitchell et al., Selectivity of nonsteroidal antiinflammatory drugs as inhibitors of constituitive and inducible cyclooxygenase, 1993, Proc. Natl. Acad. Sci. USA, 90:11693–11697.

Chan et al., Pharmacology of a selective Cyclooxygenase–2 Inhibitor, L–745,337: A Novel Nonsteroidal Anti–inflammatory Agent with an Ulcerogenic Sparing Effect in Rat and Nonhuman Primate Stomach, 1995, J. Pharmacol. Exp. Ther., 274:1531–1537.

Masferrer et al., Selective inhibition of inducible cyclooxygenase 2 in vivo is anti–inflammatory and nonulcerogenic, 1994, Proc. Natl. Acad. Sci. USA, 91:3228–3232.

Seibert et al., Pharmacological and biochemical demonstration of the role of cyclo oxygenase 2 in inflammation and pain, 1994, Proc. Natl. Acad. Sci. USA, 91:12013–12017.

Glaser et al.,Etodolac selectively inhibits human prostaglandin G/H synthase 2 (PGHS–2) versus human PGHS–1, 1995, Eur. J. Pharmacol., 281:107–111.

Sano et al., Expression of Cyclooxygenase–1 and –2 in Human Colorectal Cancer, 1995, Cancer Res., 55:3785–3789.

Rogers et al., Clinical trial of indomethacin in Alzheimer's disease, 1993, Neurology, 43:1609–1611.

*Primary Examiner*—Johann Richter
*Assistant Examiner*—Jane C. Oswecki
*Attorney, Agent, or Firm*—Arnold S. Milowsky

[57] ABSTRACT

This invention provides compounds of formula I having the structure

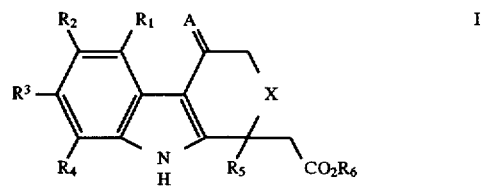

wherein $R_1$, $R_2$, $R_3$ and $R_4$ are, each, independently, hydrogen, alkyl, alkenyl, alkynyl, alkoxy, aralkoxy, trifluroalkoxy, alkanoyloxy, hydroxy, halo, trifluoromethyl, cyano, amino, mono– or di–alkylamino, alkanamido, or alkanesulfonamido;

$R_5$ is hydrogen, alkyl, alkenyl, alkoxyalkyl or alkylcycloalkyl;

$R_6$ is hydrogen, alkyl or alkenyl;

X is oxygen or carbon;

A is oxygen or NZ;

Z is hydroxyl, alkoxy, aryloxy, carboxyalkyloxy of 2–7 carbon atoms, arylamino, or alkylsulfonyamino of 1–6 carbon atoms;

or a pharmaceutically acceptable salt thereof, which are useful in the treatment of arthritic disorders, colorectal cancer, and Alzheimer's disease.

10 Claims, No Drawings

PYRANOINDOLE INHIBITORS OF COX—2

This application claims the benefit of U.S. Provisional Application No. 60/022,471, filed Jul. 26, 1996.

FIELD OF THE INVENTION

This invention is in the fields of antiinflammatory and anticancer pharmaceutical agents and specifically relates to compounds, compositions and methods for treating inflammation and inflammation-associated disorders, such as arthritis and for treating colorectal cancer.

BACKGROUND OF THE INVENTION

Prostaglandins have been shown to be involved in the pathophysiology of several chronic human diseases. They are involved as mediators of pain, edema and vascular permeability in arthritic diseases such as rheumatoid arthritis and osteoarthritis (Lewis and Kreft, *Immunopharmacol. Immunotoxicol.* 17, 607–663 (1995)). In addition, prostaglandins have been postulated to be involved in the pathophysiology of colorectal cancer (Marcus, *New Eng. J. Med.*, 333, 656–657 (1995)). Thus an agent that inhibits prostaglandin synthesis may be useful in treating these disorders.

The biosynthesis of prostaglandins was previously thought to be due to the action of a single cyclooxygenase enzyme on arachidonic acid to afford prostaglandin $H_2$ (Vane et al., *Postgrad. Med. J.*, 66 (Suppl 4), S2–S17 (1990), Lewis and Kreft, *Immunopharmacol. Immunotoxicol.* 17, 607–663 (1995)). This intermediate is subsequently transformed into the various members of the prostaglandin family by more distal enzymes. The clinical utility of cyclooxygenase inhibitors (often called NSAIDs: nonsteroidal antiinflammatory drugs) is well established in arthritic disorders (Brooks et al, *New Eng. J. Med.*, 324, 1716–1725 (1991)); however, these compounds have serious G.I. side effects due to the importance of prostaglandins in the maintenance of gastrointestinal functioning and renal blood flow (Dajani et. al., *J Physiol. Pharmacol.*, 46, 3–16 (1995); Somasundaram et al, *Scand. J. Gastroenterol.*, 30, 289–299 (1995)). Under the old paradigm of a single cyclooxygenase enzyme it appeared that the selective inhibition of prostaglandin synthesis in inflamed tissue versus inhibition of prostaglandin synthesis in G.I tissue was unlikely unless tissue specificity could be achieved.

Recently the discovery that there are two distinct cyclooxygenase enzymes has given rise to a new paradigm which may lead to compounds that have a separation of inhibition of prostaglandin synthesis in inflamed tissue from inhibition of prostaglandin synthesis in G.I tissue (Hayllar, *Lancet*, 346, 521–522 (1995), Lewis and Kreft, *Immnunopharmacol. Immunotoxicol.* 17, 607–663 (1995)). In the new paradigm the constitutive cyclooxygenase enzyme responsible for prostaglandin synthesis in G.I tissue is termed COX-1 and the inducible cyclooxygenase enzyme responsible for prostaglandin synthesis in inflamed tissue is termed COX-2. Several groups have reported that NSAIDS vary in their ability to inhibit COX-1 and COX-2 so that selective inhibition may be possible (O'Neill et al, *Molec. Pharmacol.*, 45, 245–254 (1994); Laneuville et al., *J. Pharmacol. Exp. Ther.*, 271, 927–934 (1994); Mitchell et al, *Proc Natl. Acad. Sci. USA*, 90, 11693–11697 (1993)). It is hoped that a selective COX-2 inhibitor would not only have clinical efficacy in inflammatory diseases but also would lack G.I toxicity. There is evidence from animal models to support this hypothesis (Chan et. al., *J. Pharmacol Exp.Ther.* 274, 1531–1537 (1995); Masferrer et. al., *Proc. Natl. Acad. Sci. USA*, 91, 3228–3232 (1994); Seibert et al. *Proc. Natl Acad. Sci. USA*, 91, 12013–12017 (1994)). Moreover, this may be the mechanism behind the improved G.I. safety of the NSAID etodolac which has a tenfold selectivity for inhibition of COX-2 (Glaser et. al., *Eur. J. Pharmacol.* 281, 107–111 (1995)). Thus novel COX-2 inhibitors appear as attractive targets for antiarthritic therapy with potential to reduce G.I side effects. In addition, the COX-2 enzyme has been shown to be upregulated in colorectal cancer and a selective COX-2 inhibitor may also be of use in this disease (Sano et. al., *Cancer Res.*, 55, 3785–3789 (1995)). In addition, indomethacin, a relatively non-selective inhibitor of COX-2 with adverse G.I. side effects, has been shown to be useful in the treatment of Alzheimer's disease (Rogers et. al., *Neurology*, 43, 1609–1611 (1993)) which suggests that a COX-2 selective inhibitor would be not only useful for the treatment of Alzheimer's disease but also a safer therapy with fewer G.I. side effects.

Humber et al have described the 10 step synthesis of the 4-oxo analog of the 1,3,4,9-tetrahydropyrano[3,4-b]indole, etodolac (*J. Med. Chem.* 31, 1712–1719 (1988); U.S. Pat. No. 4,686,213). The 4-oxo metabolite was active in blocking prostaglandin synthesis and had oral in vivo antiinflammatory activity. In this invention we not only describe new analogs of this compound beyond the limited scope of U.S. Pat. No. 4,686,213 but also detail an improved 4 step synthesis for preparing this metabolite as well as previously unknown 4-imino analogs and their activity against the COX-2 enzyme.

DESCRIPTION OF THE INVENTION

In accordance with this invention, there are provided COX-2 inhibitors which are useful as antiarthritic, anticancer and antiAlzheimers agents of formula I:

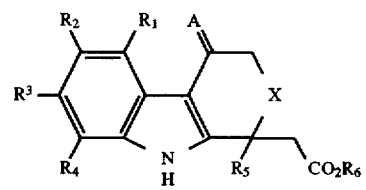

wherein $R_1$, $R_2$, $R_3$ and $R_4$ are, each, independently, hydrogen, alkyl of 1–6 carbon atoms, alkenyl of 2–7 carbon atoms, alkynyl of 2–7 carbon atoms, alkoxy of 1–6 carbon atoms, aralkoxy of 7 to 12 carbon atoms, trifluoroalkoxy, alkanoyloxy of 2–6 carbon atoms, hydroxy, halo, trifluoromethyl, cyano, amino, mono- or di-alkylamino in which each alkyl group has 1–6 carbon atoms, alkylmido of 2–6 carbon atoms, or alkylsulfonamido of 1–6 carbon atoms;

$R_5$ is hydrogen, alkyl of 1–6 carbon atoms, alkenyl of 2–7 carbon atoms, alkoxyalkyl in which each alkyl moiety has 1–6 carbon atoms or alkylcycloalkyl in which the alkyl moiety has 1–6 carbon atoms and the cycloalkyl moiety has 3–8 carbon atoms;

$R_6$ is hydrogen, alkyl of 1–6 carbon atoms or alkenyl of 2–7 carbon atoms;

X is oxygen or carbon;

A is oxygen or NZ;

Z is hydroxyl, alkoxy, aryloxy, carboxyalkyloxy of 2–7 carbon atoms, arylamino, or alkylsulfonyamino of 1–6 carbon atoms;

or a pharmaceutically acceptable salt thereof.

This invention provides both the R and S stereoisomers of the C-1 alkanoic acid, as well as to mixtures of the R and S stereoisomers. Throughout this application, the name of the product of this invention, where the absolute configuration of the C-1 alkanoic acid is not indicated, is intended to embrace both R and S enantiomers as well as mixtures of the two. The terms alkyl, alkenyl, and alkynyl include both straight chain as well as branched moieties. The term halo includes fluorine, chlorine, bromine, and iodine.

It is preferred that the aryl moiety is a phenyl group which may be optionally mono-, di-, or tri-substituted with a substituent or substituents such as alkyl of 1–6 carbon atoms, arylalkyl of 7–10 carbon atoms, alkoxy of 1–6 carbon atoms, cyano, halogen, nitro, carboalkoxy of 2–7 carbon atoms, —$CF_3$, —$OCF_3$, —$OCH_2CF_3$, amino, dialkylamino of 1–6 carbons per alkyl group, alkoxyalkyl of 2–12 carbon atoms, alkylthio of 1–6 carbon atoms, $SO_3H$, $PO_3H$, and $CO_2H$.

Preferred compounds of this invention include those in which $R_6$ is hydrogen; those in which $R_6$ is hydrogen and $R_5$ is alkyl of 1–6 carbon atoms, alkenyl of 1–6 carbon atoms, or alkoxyalkyl in which each alkyl moiety has 1–6 carbon atoms; those in which $R_6$ is hydrogen, $R_5$ is alkyl of 1–6 carbon atoms, alkenyl of 1–6 carbon atoms, or alkoxyalkyl in which each alkyl moiety has 1–6 carbon atoms, and A is oxygen; and those in which $R_6$ is hydrogen, $R_5$ is alkyl of 1–6 carbon atoms, alkenyl of 1–6 carbon atoms, or alkoxyalkyl in which each alkyl moiety has 1–6 carbon atoms, X is $CH_2$ or oxygen and A is NZ where Z is OH or $NHSO_2$alkyl in which each alkyl moiety has 1–6 carbon atoms.

The pharmaceutically acceptable salts include those derived from organic and inorganic acids such as, but not limited to: acetic, lactic, citric, tartaric, succinic, fumaric, maleic, malonic, mandelic, malic, hydrochloric, hydrobromic, phosphoric, nitric, sulfuric, methanesulfonic, toluenesulfonic and similarly known acceptable acids. Carboxylate salts, preferably alkali metal salts, for example, sodium or lithium, may also be prepared as salts of carboxylic acids where $R_6$ is hydrogen.

The compounds having the formula I as illustrated above where A, $R_1$, $R_2$, $R_3$, $R_4$, $R_5$, $R_6$ and X are as defined above and their pharmaceutically acceptable salts may be prepared by a process which comprises:

(a) oxidation of a compound having the formula II

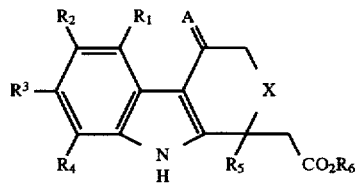

where $R_1$, $R_2$, $R_3$, $R_4$, $R_5$, $R_6$ and X are as defined above or a salt thereof so as to prepare a compound having the formula I as illustrated above in which A is oxygen and $R_1$, $R_2$, $R_3$, $R_4$, $R_5$, $R_6$ and X are as defined above or a salt thereof; or (b) reaction of a compound having the formula I where A is oxygen and R1, $R_2$, $R_3$, $R_4$, $R_5$, $R_6$ and X are as defined above or a salt thereof with a compound having the formula $H_2NZ$ where Z is as defined above to prepare a compound having formula I as illustrated above where A is NZ and $R_1$, $R_2$, $R_3$, $R_4$, $R_5$, $R_6$, and X are as defined above or a salt thereof; or (c) hydrolysis of a compound having formula I as illustrated above where A, $R_1$, $R_2$, $R_3$, $R_4$, $R_5$ and X are as defined above and $R_6$ is alkyl of 1–6 carbon atoms or alkenyl of 2–7 carbon atoms so as to form a compound having formula I as illustrated above where A, $R_1$, $R_2$, $R_3$, $R_4$, $R_5$, $R_6$ and X are as defined above and $R_6$ is hydrogen or a salt thereof.

In addition a compound of the invention may be converted into a salt thereof (or such a salt may be converted into a compound of the invention). Such a conversion may be carried out by addition of an acid or a base as appropriate.

The 4-oxo- 1,2,3,4-tetrahydro-4H-carbazole-1-alkanoic acids of this invention can be conveniently prepared by oxidation of the corresponding carbazole (prepared via Fischer indolization of the appropriate cyclohexanone with the appropriately substituted phenylhydrazine) with either 2,3-dichloro-5,6-dicyano-1,4-benzoquinone (DDQ) or 2,2, 6,6-tetramethyl-piperidine-1-oxonium tetrafluoroborate (TEMPO $BF_4$); the related 4-imino compounds can be preferably prepared by reaction of the 4-oxo esters with appropriately substituted amines followed by hydrolysis of the ester moiety (Scheme 1). The starting materials or intermediates are available commercially or can be prepared by standard literature procedures.

Scheme 1

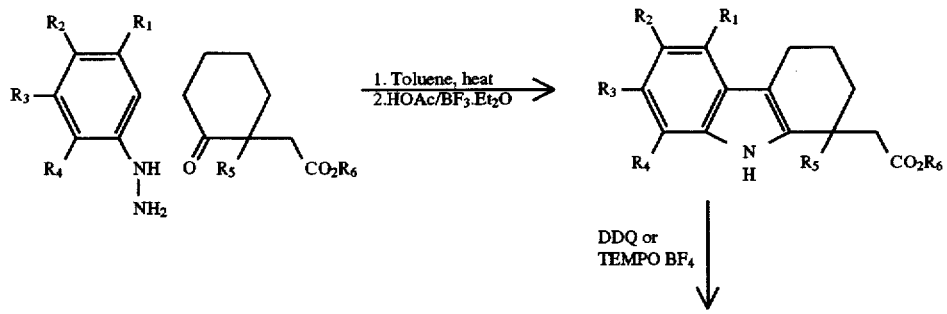

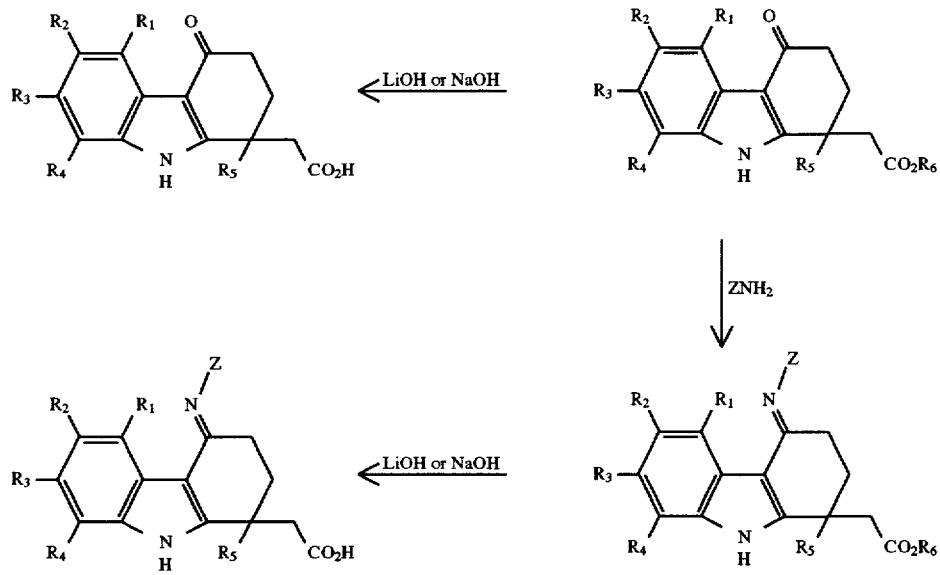

4-oxo 1,3,4,9-tetrahydropyrano[3,4-b]indole-1-alkanoic acids can be prepared by oxidation of the corresponding 1,3,4,9-tetrahydropyrano[3,4-b]indole (prepared, in turn, via cyclization of the appropriately substituted tryptophol with an alkoxy enol ether) with either 2,3-dichloro-5,6-dicyano-1,4-benzoquinone (DDQ) or 2,2,6,6-tetramethyl-piperidine-1-oxonium tetrafluoroborate (TEMPO BF$_4$); the related 4-imino analogs can be preferably prepared by reaction of the 4-oxo esters with various substituted amines followed by hydrolysis of the ester moiety (Scheme 2).

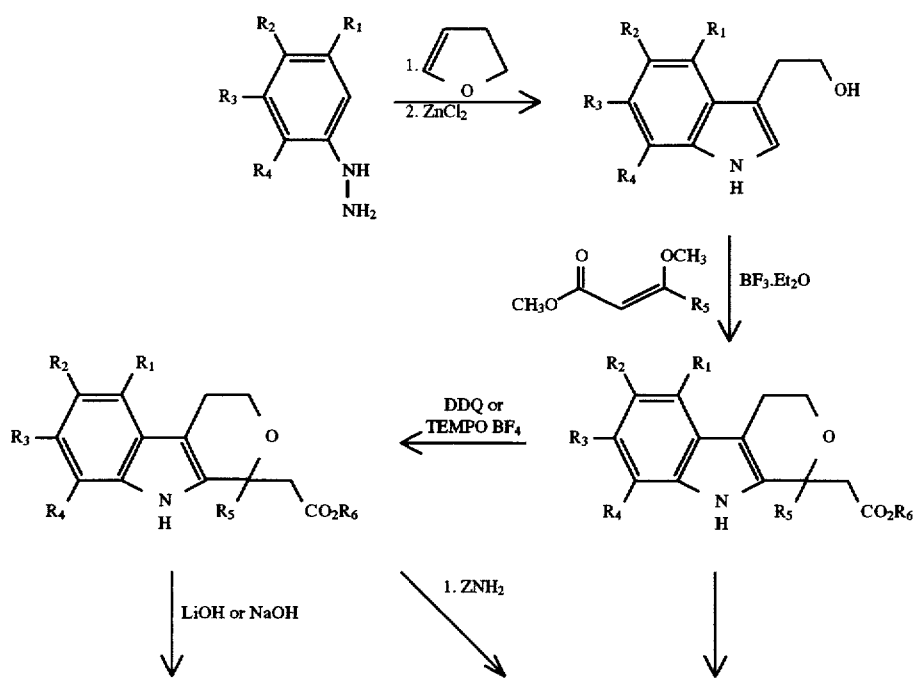

-continued
Scheme 2

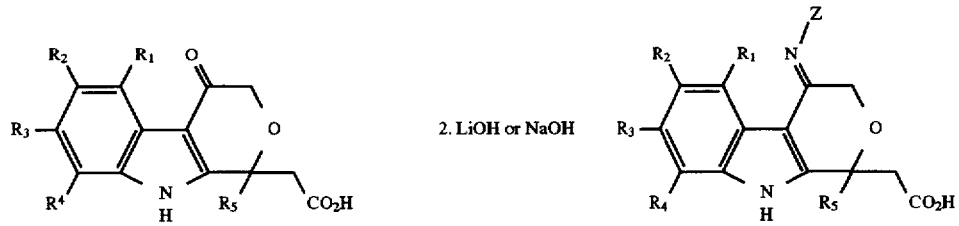

In addition, other functionalized analogs may be prepared by displacement of a bromo substituent such as shown in Scheme 3 ($R_1$=Br).

preparation as described by Glaser et al (*Eur. J. Pharmacol.* 281, 107–111 (1995)). The microsomal human recombinant enzymes were diluted with buffer (100 mM Tris, pH 7.8 at Scheme 3

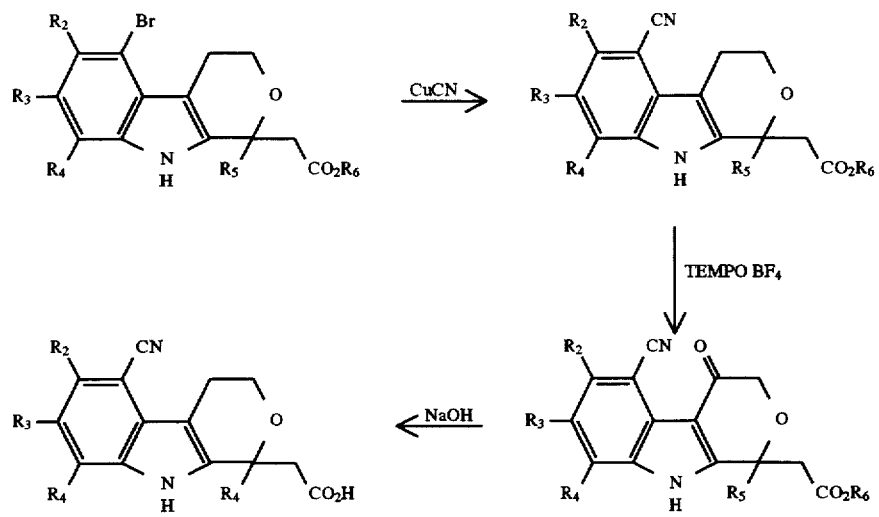

The compounds of this invention inhibit the COX-2 enzyme which is believed to be responsible for the production of high levels of prostaglandins in inflammation and colorectal cancer (Tables 1–3). It has been shown that selective inhibition of the COX-2 enzyme relative to COX-1 inhibition leads to an antiinflammatory effect without G.I. toxicity (Chan et. al., *J. Pharmacol Exp. Ther.* 274, 1531–1537 (1995); Masferrer et. al., *Proc. Natl. Acad. Sci. USA*, 91, 3228–3232 (1994); Seibert et al., *Proc. Natl. Acad. Sci. USA*, 91, 12013–12017 (1994)). Therefore, the compounds of this invention are useful for the treatment of inflammatory diseases such as rheumatoid arthritis. In addition, compounds that selectively inhibit the COX-2 enzyme are expected to have a greater margin of safety.

The compounds of this invention were evaluated for inhibition of COX-2 and COX-1 as follows: human COX-1 and COX-2 cDNAs were cloned from human monocytes, untreated and LPS treated, respectively, by RT-PCR using oligonucleotide primers based on published rhCOX-1 and rhCOX-2 sequences (Jones et al, *J. Biol. Chem.*, 268, 9049 (1993)). The cDNAs were then transfected into either Sf9 or CHO cells and subsequently converted into a microsomal 370° C.) containing 0.5 mM phenol (964 µl total volume). The enzyme preparations were preincubated with vehicle (DMSO) or compounds in DMSO (1% DMSO in final assay) for 30 min at 370° C. Excess hematin was added 1 min prior to initiation of reaction (1.25 µM final hematin) with 30 µM arachidonic acid (sodium salt). Final assay volume was 1.0 ml (100 mM Tris (pH7.8), 0.5 mM phenol, 1.25 µM hematin and 30 µM arachidonic acid at 370° C.).

The reaction was incubated for 35 s (maximum level of $PGH_2$ accumulation as determined from time course studies), and terminated by addition of 50–60 µl of $SnCl2$ (1 mg/ml) in 0.1N HCl. $PGH_2$ is quantitatively converted to $PGF_{2\alpha}$ by this reaction (50% efficiency of total conversion). The pH of each tube is adjusted to pH 3.0–3.5 with 1N NaOH and extracted twice with 1.5 ml of ethyl acetate (75–90% efficiency per extraction). Combined ethyl acetate layers were dried under $N_2$ (g) and redissolved in EIA buffer (2.0 ml), and $PGF_{2\alpha}$ was quantified by EIA.

The results of the standard pharmacological test procedure described in the preceding paragraphs were as follows:

TABLE 1

Inhibition of rhCOX-1 and COX-2 by 4-oxo-1,3,4,9-tetrahydropyrano[3,4-b]indoles

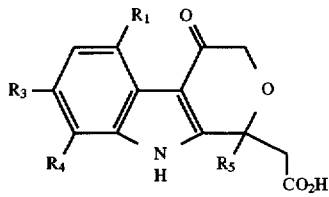

| Exam | R1 | R3 | R4 | R5 | % Inhib of rhCOX-2 (IC$_{50}$) | % Inhibition of rhCOX-1 |
|---|---|---|---|---|---|---|
| 1 | H | H | H | Et | (2.1 μM) | 42% at 90 μM |
| 2 | H | H | H | nPr | (3.2 μM) | 44% at 90 μM |
| 3 | H | H | H | CH$_2$OCH$_3$ | 8% at 3 μM | |
| 4 | H | H | Et | Et | (1.9 μM) | (>270 μM) |
| 5 | Cl | H | H | Et | (1.2 μM) | |
| 6 | Br | H | H | Et | (1.1 μM) | |
| 7 | CN | H | H | Et | 7% at 1 μM | |
| 8 | H | F | allyl | Et | (0.37 μM) | 78% at 3 μM |

$R_2$ = H for all compounds in Table 1

TABLE 2

Inhibition of rhCOX-1 and COX-2 by 4-oxo-1,2,3,4-tetrahydro-4H-carbazoles

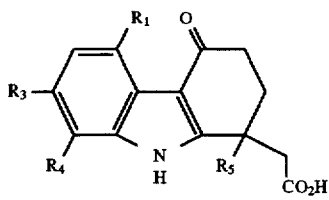

| Exam | R1 | R3 | R4 | R5 | % Inhib of rhCOX-2 (IC$_{50}$) | % Inhibn of rhCOX-1 |
|---|---|---|---|---|---|---|
| 9 | H | H | H | Et | 26% at 3 μM | |
| 10 | H | H | Et | Et | (2.0 μM) | 26% at 90 μM |
| 11 | H | H | iPr | Et | 40% at 3 μM | 85% at 90 μM |
| 12 | Cl | H | H | Et | 12% at 1 μM | 5% at 30 μM |
| 13 | F | H | F | Et | 25% at 1 μM | |
| 14 | H | F | F | Et | (0.7 μM) | 50% at 23 μM |
| 15 | F | H | F | allyl | 30% at 1 μM | |
| 16 | F | H | F | nPr | 29% at 1 μM | |
| 17 | F | F | H | nPr | 13% at 1 μM | |

$R_2$ = H for all compounds in Table 2

TABLE 3

Inhibition of rhCOX-1 and COX-2 by 4-imino-1,2,3,4-tetrahydro-4H-carbazoles and 1,3,4,9-tetrahydropyrano[3,4-b]indoles

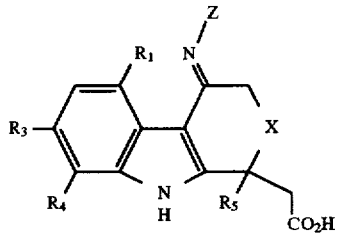

| Exam | R1 | R3 | R4 | R5 | X | Z | Inhib rhCOX-2 | % Inhib rhCOX-1 |
|---|---|---|---|---|---|---|---|---|
| 18 | H | H | Et | Et | O | OH | 50% at 3.3 µM | 96% at 90 µM |
| 19 | H | H | Et | Et | O | $NSO_2CH_3$ | 50% at 3.3 µM* | 96% at 90 µM* |
| 20 | H | H | Et | Et | $CH_2$ | OH | 18% at 1 µM | |

$R_2$ = H for all compounds in Table 3
*Sodium salt

Based on the results shown in the tables above, the compounds of this invention demonstrated high inhibition of the human COX-2 isozyme and are therefore useful for the treatment of inflammation and inflammation-associated disorders, as an anticancer agent, and other disease states where a role for the COX-2 enzyme in producing high levels of prostaglandins has been proposed. In particular, the compounds of this invention are useful in treating arthritic disorders, such as rheumatoid arthritis; Alzheimers disease; and colorectal cancer.

Certain of the examples in the claims of the invention also demonstrated high selectivity for inhibition of the human COX-2 isozyme and would be expected to have a greater margin of G.I. safety, thereby facilitating patient compliance.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets, preferably, contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount of therapeutically active compound that is administered and the dosage regimen for treating a specific arthritic disorder or colorectal cancer with the compound and/or compositions of this invention depends on a variety of factors, including the weight, age, sex, medical condition of the subject, the severity of the disease, the route and frequency of administration, and the specific compound employed, and thus may vary widely. The pharmaceutical compositions may contain active ingredient in the range of 0.1 to 2000 mg, preferably in the range of 0.5 to 500 mg and most preferably between 1 and 100 mg. Projected daily dosages of active compound are 0.01 to 100 mg/kg body weight. The daily dose of can be administered in one to four doses per day.

The following examples illustrate the preparation of representative compounds of this invention.

EXAMPLE 1

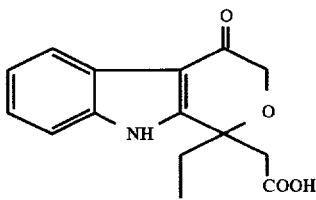

(1-Ethyl-4-oxo-1,3,4,9-tetrahydro-pyrano[3,4-b]indol-1-yl)-acetic acid

To a stirred solution at room temperature under nitrogen of 1-ethyl-1,3,4,9-tetrahydro-pyrano[3,4-b]indol-1-yl)-acetic acid methyl ester (Demerson et al *J. Med. Chem.* 18, 189–191 (1975), 0.271 g, 1 mmol) in 20 ml of dichloromethane-methanol mixture (9:1) was added 2,3-dichloro-5,6-dicyano-1,4-benzoquinone (0.5 g, 2.2 mmol). After 30 min of stirring when TLC showed ~90% conversion, the mixture was diluted with water (25 ml), ethyl acetate (50 ml) and sodium sulfite (10 ml of a 10% solution). The resulting mixture was stirred for ~10 min (until substantial discoloration occurred) and diluted with 1N NaOH solution (20 ml). Extraction with ethyl acetate (50 ml×3) followed by evaporation of the solvent gave a light brown powder. Purification by flash chromatography (45:55 ethyl acetate:hexane) afforded 0.2 g (70%) of the methyl ester which gave after hydrolysis (48 h, MeOH/2.5N NaOH), 0.181 g (95%) of the desired product as a solid, m.p. 235°–238° C.

Analysis for: $C_{15}H_{15}NO_4$ Calculated: C, 65.93; H, 5.53; N, 5.13. Found: C, 64.81; H, 5.66 ; N, 4.85.

$^1$H NMR (400 MHz, DMSO): δ12.24 (s, 1H), 12.04 (s, 1H), 7.2–8.1 (m, 4H), 4.2–4.32 (dd, 2H), 2.8–3.1 (dd, 2H), 1.9–2.2 (m, 2H), 0.83 (t, 3H).

IR (KBr, cm$^{-1}$): 3420, 2960, 1720, 1620, 1470.

MS [(−)FAB m/z]: (M−H)$^-$272.

EXAMPLE 2

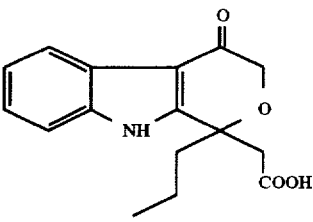

(1-Propyl-4-oxo-1,3,4,9-tetrahydro-pyrano[3,4-b]indol-1-yl)-acetic acid

The title compound was prepared from 1-propyl-1,3,4,9-tetrahydro-pyrano[3,4-b]indol-1-yl)-acetic acid methyl ester (Demerson et al *J. Med. Chem.* 18, 189–191 (1975), 0.286 g, 1 mmol) using the method of Example 1. Purification by flash chromatography (45:55 ethyl acetate:hexane) afforded 0.226 g (75 %) of the methyl ester which gave after hydrolysis (48 h, MeOH–2.5N NaOH) 0.205 g (95 %) of the desired product as a solid, m.p. 206°–208° C.

Analysis for: $C_{16}H_{17}NO_4$ Calculated: C, 66.89; H, 5.96; N, 4.87. Found: C, 66.74; H, 5.95; N, 4.73.

$^1$H NMR (400 MHz, DMSO): δ12.22 (s, 1H), 12.02 (s, 1H), 7.1–8.0 (m, 4H), 4.2–4.4 (dd, 2H), 2.8–3.1 (dd, 2H), 1.9–2.2 (m, 2H), 1.1–1.4 (m, 2H), 0.85 (t,3H).

IR (KBr, cm$^{-1}$): 3400, 2950, 1710, 1620, 1460.

MS [(−)FAB m/z]: (M−H)$^-$287.

EXAMPLE 3

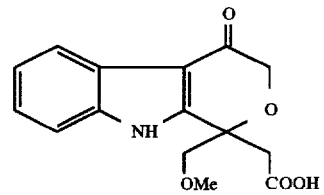

(1-Methoxymethyl-4-oxo-1,3,4,9-tetrahydro-pyrano[3,4-b]indol-1-yl)-acetic acid

A. (1-Methoxymethyl-1,3,4,9-tetrahydro-pyrano[3,4-b]indol-1-yl)-acetic acid

To a stirred solution of tryptophol (0.8 g, 5 mmol) and methyl 3,4-dimethoxy-2-butenoate (0.96 g, 6 mmol) in dichloromethane (15 ml, under inert atmosphere) in a 50 ml flask equipped with a magnetic stirrer at room temperature under nitrogen was added dropwise boron trifluoride etherate (0.15 ml, 1.22 mmol). After completion of the reaction (~2 h, monitoring by TLC), the mixture was diluted with 50 ml of dichloromethane and quenched with 50 ml of pH 7 buffer. The layers were separated and the aqueous layer was washed with dichloromethane. The combined organic fractions were washed with brine and dried over sodium sulfate. Purification by flash chromatography (hexane:EtOAc=3:1) afforded 1.15 g (80%) of colorless crystals that were subjected to hydrolysis in 40 mL of 3:1 mixture MeOH: 1N NaOH. After the reaction was complete (24 h., monitored by TLC), methanol was removed in vacuo, the mixture was diluted with water (30 mL), and the neutral components were extracted with ethyl acetate (25 mL×2). The water layer was acidified with 1N HCl and the product extracted with ethyl acetate (50 mL×3). The crude material obtained after evaporation of the solvent was redissolved in dichloromethane and precipitated with hexane. Final filtration afforded, after drying, 1.04 g (95%) of the desired product as a solid, m.p. 135°–140° C.

Analysis for: $C_{15}H_{17}NO_4$ Calculated: C, 65.45; H, 6.18; N, 5.09. Found: C, 64.84; H, 6.25; N, 4.97.

$^1$H NMR (400 MHz, DMSO): δ11.97 (s, 1H, broad), 10.62 (s, 1H), 6.9–7.2 (m, 4H), 3.98 (m, 2H), 3.6–3.8 (dd, 2H), 3.3 (s, 3H), 2.8 (dd, 2H)

IR (KBr, cm$^{-1}$): 3320, 2900, 1700, 1450.

MS (EI m/z): [M$^+$] 275, 244, 230.

B. (1-Methoxymethyl-4-oxo-1,3,4,9-tetrahydro-pyrano[3,4-b]indol-1-yl)-acetic acid To a stirred solution at room temperature under nitrogen of (1-methoxymethyl-1,3,4,9-tetrahydro-pyrano[3,4-b]indol-1-yl)-acetic acid methyl ester (0.29 g, 1 mmol) in 5 ml of benzene and 5 ml of pH 4 buffer was added dropwise over 1.5 h a solution of 2,3-dichloro-5,6-dicyano-1,4-benzoquinone (1.135 g, 5 mmol) in benzene (30 ml). After 8 h of stirring when the TLC showed ~90% conversion, the mixture was diluted with water (25 ml), ethyl acetate (50 ml), and sodium sulfite (10 ml of a 10% solution). The resulting mixture was stirred for ~10 min (until substantial discoloration occurred), and diluted with 1N NaOH solution (20 ml). Extraction with ethyl acetate (50 ml×3), followed by evaporation of the solvent gave a light brown powder. Purification by flash chromatography (45:55 ethyl acetate:hexane) afforded 0.195 g (65 %) of methyl ester which gave after hydrolysis (24 h, MeOH–1N NaOH), 0.170 g (90%) of the title compound as a solid, m.p. 135°–1400° C.

Analysis for: $C_{15}H_{15}NO_5$ Calculated: C, 63.36; H, 5.65; N, 4.62. Found: C, 61.60; H, 5.16; N, 4.70.

$^1$H NMR (400 MHz, DMSO): δ12.0 (s, 1H), 7.18–7.9 (m, 4H), 4.0–4.4 (dd, 2H), 3.7–3.9 (dd, 2H), 3.26 (s, 3H), 2.8–3.2 (dd, 2H)

IR (KBr, cm$^{-1}$): 3360, 2900, 1720, 1640, 1460.

MS (EI): 289, 244.

EXAMPLE 4

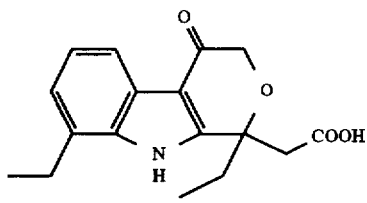

1,8-Diethyl-4-oxo-1,3,4,9-tetrahydro-pyrano [3,4-b] indole-1-acetic acid

A. 1,8-Diethyl-1,3,4,9-tetrahydro-pyrano [3,4-b] indole-1-acetic acid methyl ester 1,8-Diethyl-1,3,4,9-tetrahydro-pyrano [3,4-b]-1-indole acetic acid (5.0g, 17.4 mmol) (Demerson et al *J. Med. Chem.* 19, 391–395 (1976)) was dissolved in MeOH and $H_2SO_4$ (2.12 g, 21.6 mmol) was added dropwise. After overnight stirring, the mixture was concentrated, and the precipitate filtered, washed with water, and dried in vacuo to yield the title compound as a solid, 4.68 g. m.p. 130°–132° C.

B. 1,8-Diethyl-4-oxo-1,3,4,9-tetrahydro-pyrano [3,4-b] indole-1-acetic acid methyl ester The ester produced in step A (0.5g, 1.66 mmol) was dissolved in 5 ml of a 90% THF/water solution, and to this was added 2,3-dichloro-5,6-dicyano-1,4-benzoquinone (0.75 g, 3.3 mmol., previously dissolved in 5 ml THF). This mixture was stirred overnight. The solvent was evaporated and 50 ml of ethyl acetate was added. The organic phase was extracted sequentially with 2.5N NaOH, distilled water and brine. The organic layer was separated, dried (MgSO$_4$) and evaporated to produce 0.56 g of crude oil. The oil was flash chromatographed using $CH_2Cl_2$—EtOAc 98-2 as eluant to yield 0.15 g of the desired product as a solid, m.p. 187°–189° C.

Analysis for: $C_{18}H_{21}NO_4$ Calculated: C, 68.55; H, 6.71; N 4.44. Found: C, 68.54; H, 6.55; N, 4.44.

C. 1,8-Diethyl-4-oxo-1,3,4,9-tetrahydro-pyrano-[3,4-b] indole-1-acetic acid

A solution of the product produced in step B (1.25 g, 3.9 mmol), $K_2CO_3$ (3.5 g, 25.3 mmol) and 60 ml MeOH/H$_2$O 1:1 was refluxed for 3 h. The methanol was evaporated, and the aqueous residue acidified to pH 1 using 6N HCl. The aqueous phase was extracted with EtOAc. The organic phase was washed with water, dried (MgSO4), and evaporated to produce a crude glass which was recrystallized from EtOAc-hexane to afford 1.1 g of the title compound as a solid, m.p. 198°–201° C.

Analysis for: $C_{17}H_{19}NO_4$ Calculated: C, 67.76; H, 6.36; N 4.65. Found: C, 67.38; H, 6.33; N, 4.51.

EXAMPLE 5

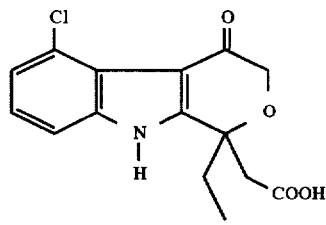

(5-Chloro-1-ethyl-4-oxo-1,3,4,9-tetrahydro-pyrano [3,4-b]indol-1-yl)-acetic acid To a solution of 5-chloro-1 ethyl-1,3,4,9-tetrahydropyrano[3,4-b|indole-1-acetic acid (Demerson et al *J. Med. Chem.* 19, 391–395 (1976), 0.990 g, 3.37 mmole) in methanol (30 ml) was added concentrated HCl (0.325 g), and the mixture was stirred at room temperature overnight. The methanol was removed and water added to the residue. 1N NaOH was added and the mixture extracted with ethyl acetate. The combined extracts were dried (MgSO$_4$), and concentrated to a gummy solid which was triturated (ethyl acetate-hexane) to afford 0.425 g solid. The solid was dissolved in 9:1 tetrahydrofuran-water (5 ml) and treated with a solution of TEMPO$^+$ BF$_4^-$ (0.663 g, 2.72 mmole) in 9:1 tetrahydrofuran-water (5 ml). After stilling for one hour, the mixture was concentrated, and water added to the residue. The mixture was extracted with ether, dried (MgSO$_4$) and concentrated to an oil. Flash chromatography (eluting with 95:5 methylene chloride-ethyl acetate) afforded 0.240 g of product which was hydrolyzed by treating with 1N LiOH (3 ml) and THF (6 ml) overnight. After the solvent was removed, water was added to the residue and this extracted with methylene chloride. The aqueous layer was acidified (pH 2) and the resulting solid removed, extracted into ethyl acetate, dried (MgSO$_4$), and concentrated. The solid was recrystallized (ethyl acetate-hexane) affording a pink powder (0.096 g), m.p. 240°–243° C.

Analysis for: $C_{15}H_{14}ClNO_4$ Calculated: C, 58.55; H, 4.59; N, 4.55. Found: C, 58.21; H, 4.44; N, 4.41.

EXAMPLE 6

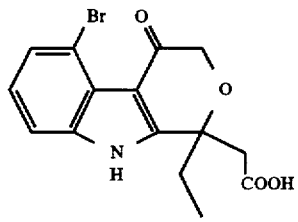

(5-Bromo-1-ethyl-4-oxo-1,3,4,9-tetrahydro-pyrano [3,4-b]indol-1-yl)-acetic acid

A. 4-(3-Bromophenylhydrazono)-1-butanol

Under anhydrous conditions a solution of 3-bromophenylhydrazine hydrochloride (22.5 g, 100 mmol) and 2,3-dihydrofuran (7.55 ml, 100 mmol) in 200 ml of dry THF was stirred at ambient temperature for 3 h. The reaction mixture was partitioned between EtOAc and H$_2$O. The organic phase was washed with H$_2$O and brine. After drying (Na$_2$SO$_4$), the solvent was evaporated to give 25.6 g of the product as a brown oil. The product was of suitable purity for use in the next step.

¹H NMR (DMSO-d₆, 300 MHz): ∂1.6 (m, 2H, CH₂CH₂CH₂), 2.2 (m, 2H, CHCH₂), 3.15 (m, 2H, CH₂OH), 6.45+6.8 (m, 2H,vinyl H+ArH), 7.05 (m, 2H, ArH), 7.2 (m, 1H, ArH), 9.25+9.85 (s, 1H, NH).

B. 1:1 Mixture of 4-bromotryptophol and 5-bromotryptophol

Under an atmosphere of nitrogen, a mixture of the crude hydrazone (25.4 g, 98.8 mmol, prepared as described in Step A) and zinc chloride (27.2 g, 200 mmol) in 200 ml of ethylene glycol was heated at 160° C. for 3 h. Upon cooling the reaction mixture was partitioned between Et₂O and dilute HCl. The organic phase was washed with H₂O and brine. After drying (Na₂SO₄), the solvent was evaporated to afford crude product. Highly polar impurities were removed by dissolving the crude product in CH₂Cl₂ and passing the solution through a pad of silica gel. Removal of the solvent afforded 22.7 g of a 1:1 mixture of 4 and 5 bromo compounds as a brown oil.

¹H NMR (DMSO-d₆, 300 MHz): ∂2.8 (t, 1H, ArCH₂C), 3.05 (t, 1H, ArCH₂C), 3.65 (m, 2H, OCH₂C), 6.9–7.5 (m, 4H, ArH), 10.9 (s, 0.5H, NH), 11.15 (s, 0.5H, NH).

C. 5-Bromo-1-ethyl-1,3,4,9-tetrahydropyrano[3,4-b]indole-1-acetic acid methyl ester Under anhydrous conditions, a solution of the mixture of tryptophols (22.6 g, 94.1 mmol, prepared as described in Step B), and methyl 3 methoxy- 2 pentenoate (13.5, 94.1 mmol) in 200 ml of dry CH₂Cl₂ was treated dropwise with boron trifluoride etherate (13.35 g, 94.1 mmol ) via syringe. The solution was stirred at ambient temperature for 2 h, and then washed with saturated NaHCO₃ and brine. Upon drying (Na₂SO₄), the organic phase was passed through a pad of silica gel. The filter cake was washed with additional CH₂Cl₂ and the combined organic layer was evaporated to provide 23 g of product as a mixture of regioisomers. The title compound was isolated via flash chromatography (silica gel, toluene-EtOAc, 9:1) to provide 1.4 g of the tide compound, m.p 118°–119° C. An additional 3.6 g of product was obtained by recrystallizing the recovered mixed products from Et₂O and petroleum ether and seeding with pure product.

Analysis for: C₁₆H₁₈BrNO₃ Calculated: C, 54.56; H, 5.15; N, 3.98. Found: C, 54.34; H, 5.07; N, 3.98.

¹HNMR (DMSO-d₆, 400 MHz): δ0.615 (t, 3H, CCH₃), 1.95 (q, 2H, CCH₂CH₃), 2.76 (d, 1H, CCH₂CO), 2.96 (m, 3H, CCH₂), 3.32 (s, 3H, OCH₃), 3.9 (m, 2H, CCH₂O), 6.93 (t, 1H, ArH), 7.11 (d, 1H, ArH), 7.32 (d, 1H, ArH), 11.148 (s, 1H, NH).

MS (m/z, EI): 351/353 (M)⁺, 322/324 (M–C₂H₅)⁺, 278/280 (b.p., M–CH₂COOH)⁺.

D. 5-Bromo-1-ethyl-4-oxo-1,3,4,9-tetrahydropyrano[3,4-b]indole-1-acetic acid methyl ester A solution of the ester (0.352 g, 1.0 mmol, prepared as described in Step C), in 10 ml of CH₃CN—H₂O (9:1, v/v) was added dropwise to a stirred solution of TEMPO-BF₄ in 10 mL of CH₃CN—H₂O (9:1, v/v). Stirring was continued for 3 hours, and the reaction mixture was concentrated in vacuo. The residue was partitioned between Et₂O and H₂O. The organic phase was washed with brine and dried (Na₂SO₄). Removal of solvent afforded a yellow oil which was purified by flash chromatography (silica gel, hexane-EtOAc 2:1) to give 0.11 g of product as an off white solid.

¹H NMR (DMSO-d₆, 400 MHz): ∂0.817 (t, 3H, CCH₂CH₃), 1.98 (m, 1H, CCH₂CH₃), 2.16 (m, 1H, CCH₂CH₃), 2.93 (d, 1H, CCH₂CO), 3.19 (d, 2H, CCH₂CO), 3.529 (s, 3H, OCH₃), 4.23 (q, 2H, CCH₂O), 7.15 (t, 1H, ArH), 7.41 (d, 1H, ArH), 7.49 (d, 1H, ArH), 12.36 (s, 1H, NH).

MS (m/z, EI): 365/367 (M)⁺, 336/338 (M–C₂H₅)⁺, 276/278 (b.p., M–CH₂COOCH₃)⁺.

E. (5-Bromo-1-ethyl-4-oxo-1,3,4,9-tetrahydro-pyrano[3,4-b]indol-1-yl)-acetic acid 0.33 EtOAc+0.16 Et₂O A solution of the ester (0.10 g, 0.27 mmol, prepared as described in Step D) in 3 ml of ethanol and 1 ml of 1N NaOH was stirred at ambient temperature overnight. The solvent was evaporated and the residue partitioned between Et₂O and H₂O. The aqueous phase was separated and acidified with 1N HCl. The mixture was extracted with Et₂O. The organic phase was dried with Na₂SO₄ and the solvent removed to provide crude product which was recrystallized from Et₂O to afford the title compound (0.04 g, 44%, white solid).

Analysis for: C₁₅H₁₄BrNO₄+0.33 EtOAc+0.16 Et₂O Calculated: C, 51.82; H, 4.68; N, 3.56. Found: C, 51.88; H, 4.65; N, 3.47.

¹H NMR (DMSO-d₆, 400 MHz): ∂0.821 (t, 3H, CCH₂CH₃), 2.00 (m, 1H, CCH₂CH₃), 2.15 (m, 1H, CCH₂CH₃), 2.82 (d, 1H, CCH₂CO), 3.08 (d, 2H, CCH₂CO), 4.235 (q, 2H, CCH₂O), 7.14 (t, 1H, ArH), 7.40 (d, 1H, ArH), 7.48 (d, 1H, ArH), 12.25 (s,1H, COOH), 12.357 (s, 1H, NH).

MS (m/z, EI):351/353 (M⁺), 322/324, 306/308.

EXAMPLE 7

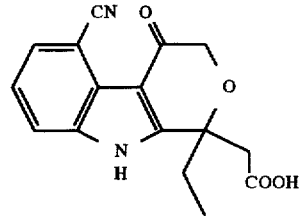

5-Cyano-1-ethyl-4-oxo-1,3,4,9-tetrahydropyrano[3,4-b]indole-1-acetic acid

A. 5-Cyano-1-ethyl-1,3,4,9-tetrahydropyrano[3,4-b]indole-1-acetic acid methyl ester Under an atmosphere of nitrogen, a solution of the compound of Example 6 (0.409 g, 1.26 mmol) and copper (I) cyanide (0.202 g, 2.27 mmol) in 10 ml of N-methyl-2-pyrrolidinone was heated at 170° C. for 5 h. Upon cooling the reaction mixture was partitioned between EtOAc and H₂O. The mixture was vacuum filtered to remove dark solids. The layers were separated and the organic phase was washed 2 times with H₂O and brine. After drying (Na₂SO₄), the solvent was evaporated to provide 0.50 g of crude solid which was purified by flash chromatography (silica gel, hexane-EtOAc 2:1) to give 0.145 g of the title compound.

¹H NMR (DMSO-d₆, 400 MHz): ∂0.642 (t, 3H, CCH₃), 1.958 (q, 2H, CCH₂CH₃), 2.78 (d, 1H, CCH₂CO), 2.86 (m, 2H, CCH₂), 2.99 (d, 1H, CCH₂CO), 3.53 (s, 3H, OCH₃), 3.9 (m, 2H, CCH₂O), 7.18 (t, 1H, ArH), 7.44 (d, 1H, ArH), 7.66 (d, 1H, ArH), 11.482 (s, 1H, NH).

MS |EI, m/z|: 298 (M⁺), 269 (M–C₂H₅)⁺, 225 (M–CH₂CO₂Me)⁺, 195

B. 5-Cyano-1-ethyl-4-oxo-1,3,4,9-tetrahydropyrano[3,4-b]indole-1-acetic acid methyl ester A solution of the ester (0.155 g, 0.52 mmol, prepared as described in Step A) in 5 ml of CH₃CN—H₂O (9:1, v/v) was added dropwise to a stirred solution of TEMPO-BF₄ in 5 ml of CH₃CN—H₂O (9:1, v/v). Stirring was continued for 48 h and the reaction mixture concentrated in vacuo. The residue was partitioned between Et₂O and H₂O. The organic phase was washed with brine and dried (Na₂SO₄). Removal of solvent provided a yellow oil which was purified by flash chromatography (silica gel, hexane-EtOAc 2:1) to afford 0.110 g of product as an off white solid.

¹H NMR (DMSO-d₆, 400 MHz): ∂0.837 (t, 3H, CCH₃), 1.97+2.17 (m, 2H, CCH₂CH₃), 2.97 (d, 1H, CCH₂CO), 3.21 (d, 1H, CCH₂CO), 3.52 (s, 3H, OCH₃), 4.29 (m, 2H, COCH₂O), 7.40 (t, 1H, ArH), 7.68 (d, 1H, ArH), 7.83 (d, 1H, ArH), 12.63 (s, 1H, NH).

MS (EI, m/z): 312 (M)⁺, 283 (M–C₂H₅)⁺, 239 (M–CH₂COOCH₃)⁺.

C. 5-Cyano-1-ethyl-4-oxo-1,3,4,9-tetrahydropyrano[3,4-b]indole-1-acetic acid

A solution of the ester (0.11 g, 0.35 mmol, prepared as described in Step B), in 3 ml of ethanol and 0.5 ml of 1N NaOH was stirred at ambient temperature overnight. The solvent was evaporated and the residue partitioned between Et₂O and H₂O. The aqueous phase was separated and acidified with 1N HCl. The mixture was extracted with Et₂O. The organic phase was dried with Na₂SO₄ and the solvent removed to provide the crude product as an oil. Trituration with Et₂O afforded the title compound (0.061 g, 58%) as a white solid.

¹H NMR (DMSO-d₆, 400 MHz): ∂0.841 (t, 3H, CCH₃), 2.01 (m, 1H, CCH₂CH₃), 2.16 (m, 1H, CCH₂CH₃), 2.87 (d, 1H, CCH₂CO), 3.10 (d, 1H, CCH₂CO), 4.29 (m, 2H, COCH₂O), 7.39 (t, 1H, ArH), 7.67 (d, 1H, ArH), 7.83 (d, 1H, ArH), 12.29 (s, 1H, NH), 12.63 (s, 1H, COOH).

MS [EI, m/z]: 298 (M⁺), 269 (M–C₂H₅)⁺, 253 (b.p).

EXAMPLE 8

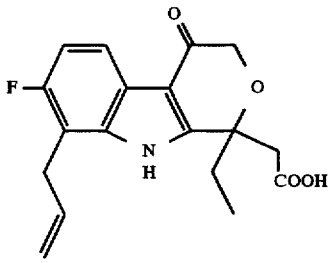

8-Allyl-1-ethyl-7-fluoro-4-oxo-1,3,4,9-tetrahydropyrano[3,4-b]indole-1-acetic acid A. 8-Allyl-1-ethyl-7-fluoro-1,3,4,9-tetrahydropyrano[3,4-b]indole-1-acetic acid methyl ester A solution of 8-allyl-1-ethyl-7-fluoro-1,3,9-trihydropyrano[3,4-b]indole-1-acetic acid (0.2 g, 0.63 mmol, Hughes et al *J. Heterocycl. Chem.* 27, 2151–2163 (1990)) in 20 ml CH₃OH was treated portionwise with a 10% solution of trimethylsilyldiazomethane until a slight yellow color persisted. The solvent was removed to give 0.21 g of the product as a light yellow oil.

¹H NMR (DMSO-d₆, 300 MHz): ∂0.6 (t, 3H, CCH₂CH₃), 1.95 (m, 2H, CCH₂CH₃), 2.6 (m, 2H, CCH₂), 2.78 (d, 1H, CCH₂CO), 2.95 (d, 2H, CCH₂CO), 3.5 (s, 3H, OCH₃), 3.6 (d, 2H, CH₂CH=CH₂), 3.9 (m, 2H, CCH₂O), 5.0 (m, 2H, CH₂CH=CH₂), 5.95 (m, 1H, CH₂CH=CH₂), 6.8 (m, 1H, ArH), 7.25 (m, 1H, ArH), 10.61 (s, 1H, NH).

B. 8-Allyl-1-ethyl-7-fluoro-4-oxo-1,3,4,9-tetrahydropyrano[3,4-b]indole-1-acetic acid methyl ester A solution of the ester (0.21 g, 0.63 mmol, prepared as described in Step A), in 10 ml of CH₃CN—H₂O (9:1, v/v) was added dropwise to a stirred solution of TEMPO-BF₄ in 10 ml CH₃CN—H₂O (9:1, v/v). Stirring was continued for 2 h and the reaction mixture was concentrated in vacuo. The residue was partitioned between Et₂O and H₂O. The organic phase was washed with brine and dried (Na₂SO₄). Removal of solvent provides a yellow oil which was purified by flash chromatography (silica gel, hexane- EtOAc 2:1) to give 0.18 g of product as an off white solid.

¹H NMR (DMSO-d₆, 400 MHz): ∂0.808 (t, 3H, CCH₂CH₃), 1.96 (m, 1H, CCH₂CH₃), 2.23 (m, 1H, CCH₂CH₃), 2.91 (d, 1H, CCH₂CO), 3.266 (d, 2H, CCH₂CO), 3.51 (s, 3H, OCH₃), 3.66 (d, 2H, CH₂CH=CH₂), 4.25 (q, 2H, CCH₂O), 4.97 (m, 2H, CH₂CH=CH₂), 5.98 (m, 1H, CH₂CH=CH₂), 7.05 (m, 1H, ArH), 7.78 (m, 1H, ArH), 11.719 (s, 1H, NH).

¹³C NMR (DMSO-d₆, 400 MHz): ∂188.959, 169.335, 158.6097, 156.25, 153.73, 135.64, 135.557, 135.132, 119.998, 119.2099, 119.1113, 115.46, 110.63 . . .

MS (EI, m/z): 345 (M)⁺, 316 (M–C₂H₅)⁺, 272 (b.p., M–CH₂COOCH₃)⁺.

C. 8-Allyl-1-ethyl-7-fluoro-4-oxo-1,3,4,9-tetrahydropyrano[3,4-b]indole-1-acetic acid A solution of the ester (0.19 g, 0.55 mmol, prepared as described in Step B), in 3 ml of ethanol and 1 ml of 1N NaOH was stirred at ambient temperature overnight. The solvent was evaporated and the residue partitioned between Et₂O and H₂O. The aqueous phase was separated and acidified with 1N HCl. The mixture was extracted with Et₂O. The organic phase was dried with Na₂SO₄ and the solvent removed to provide 0.12 g of crude product which was recrystallized from Et₂O-hexane to afford the title compound (0.10 g, 55%, mp −232°–234° C., off white solid).

Analysis for: C₁₈H₁₈FNO₄ Calculated: C, 65.25; H, 5.48; N, 4.23. Found: C, 64.97; H, 5.45; N, 4.15.

¹H NMR (DMSO-d₆, 400 MHz): ∂0.809 (t, 3H, CCH₂CH₃), 1.99 (m, 1H, CCH₂CH₃), 2.21 (m, 1H, CCH₂CH₃), 2.79 (d, 1H, CCH₂CO), 3.17 (d, 2H, CCH₂CO), 3.66 (d, 2H, CH₂CH=CH₂), 4.255 (q, 2H, CCH₂O), 4.97 (m, 2H, CH₂CH=CH₂), 5.98 (m, 1H, CH₂CH=CH₂), 7.05 (m, 1H, ArH), 7.78 (m, 1H, ArH), 11.708 (s, 1H, NH), 12.208 (s, 1H, COOH).

MS (EI, m/z): 331 (M)⁺, 302 (M–C₂H₅)⁺, 272 (M–CH₂COOCH₃)⁺.

EXAMPLE 9

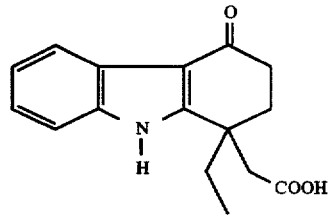

[1-Ethyl-4-oxo-2,3,4,9-tetrahydro-1H-(carbazol-1-yl)]-acetic acid

To a solution of 1-ethyl-1,2,3,4-tetrahydro-carbazole-1-acetic acid (Asselin et al *J. Med. Chem.* 19, 787–792 (1976), 0.289 g (1.12 mmole)) in methanol (10 ml) was added concentrated sulfuric acid (0.029 g) and the mixture was stirred at room temperature overnight. The methanol was removed and water added to the residue. 1N NaOH was added and the mixture extracted with ethyl acetate. The combined ethyl acetate extracts were dried (MgSO₄) and concentrated to the oily ester was dissolved in 9:1 tetrahydrofuran-water (3 ml) and chilled to 0° C. 2,3-

Dichloro-5,6-dicyano-1,4-benzoquinone (0.130 g, 0.574 mmole) was dissolved in tetrahydrofuran (1.1 ml) and added dropwise to the chilled solution. After 2 h the solvent was removed and the residue taken into ethyl acetate, washed several times with 1N NaOH, dried (MgSO$_4$) and concentrated to an oil. Flash chromatography (eluting with 2% ethyl acetate-methylene chloride) affords the ester which was hydrolyzed to the tide compound utilizing the method of Example 5 (LiOH, H$_2$O/THF). The tide compound was obtained as a white solid (0.077 g), m.p. 214°–216° C.

Analysis for: C16 H17 N O$_3$. Calculated: C, 70.83; H, 6.32; N, 5.16. Found: C, 70.54; H, 6.41; N, 5.10.

EXAMPLE 10

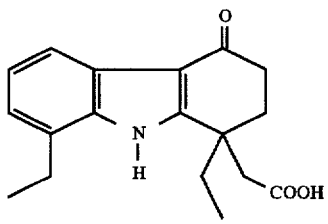

[1,8-Diethyl-4-oxo-2,3,4,9-tetrahydro-1H-(carbazol-1-yl)]-acetic acid

The title compound was prepared according to the method of Example 9 using 0.490 g (1.7 mmole) of 1,8-diethyl-1, 2,3,4-tetrahydrocarbazole-1-acetic acid (Asselin et al., *J. Med. Chem* 19, 787–792 (1976)). The title compound was obtained as a white powder (0.197 g), m.p. 212°–214° C.

Analysis for: C$_{18}$ H$_{21}$ N O$_3$ Calculated: C, 72.22; H, 7.07; N, 4.68. Found: C, 72.29; H, 7.03; N, 4.61

EXAMPLE 11

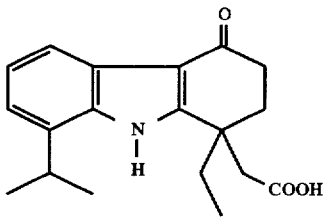

[1-Ethyl-8-isopropyl-4-oxo-2,3,4,9-tetrahydro-1H-(carhazol-1-yl)]-acetic acid

The title compound was prepared according to the method of Example 9 using 0.490 (1.71 mmole) of 1,8-diethyl-1,2, 3,4-tetrahydrocarbazole-1-acetic acid (Asselin et al., *J. Med. Chem* 19, 787–792 (1976)). The title compound was obtained as a light yellow solid (0.027 g, 55%), having a melting point of 240°–242° C.

Analysis for: C$_{19}$ H$_{23}$ N O$_3$ Calculated: C, 72.82; H, 7.40; N, 4.47. Found: C, 72.24; H, 7.51; N, 4.26.

EXAMPLE 12

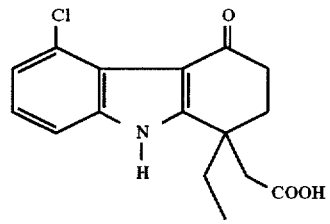

[1-Ethyl-5-chloro-4-oxo-2,3,4,9-tetrahydro-1H-(carbazol-1-yl)]-acetic acid

A. [1-Ethyl-5-chloro-2,3,4,9-tetrahydro-1H-(carbazol-1-yl)] acetic acid methyl ester A solution of 3-chlorophenylhydrazine (154 mmol) and 27.9 g of methyl 1-ethyl-2-oxocyclohexaneacetate (Asselin et al., *J. Med. Chem.* 19, 787–792 (1976), 140.6 mmol) in toluene (Dean-Stark trap) was refluxed for 43 hr. Removal of the solvent afforded 56.5 g of the crude hydrazone which was cyclized by refluxing for 1.5 h in 300 ml acetic acid containing 17 ml of BF$_3$ etherate. The reaction mixture was then cooled and poured into 750 ml of ice/water and extracted with 3×200 ml Et$_2$O. The combined ether extract was washed subsequently with 100 ml H$_2$O, 2×115 ml 0.5N HCl, 2×100 ml 2.5N NaOH (100 ml H$_2$O was added to separate layers) and 115 ml H$_2$O, dried over MgSO$_4$ and evaporated to provide 39.5 g of a red liquid. Column chromatography (silica gel, eluting with CH$_2$Cl$_2$) gave a 1:1 mixture of the 5 and 7 chloro isomeric esters which were separated by HPLC (hexane/ethyl acetate gradient) to afford the pure 5-chloro ester, m.p. 101°–104° C. (note the 7-chloro ester was a liquid).

B. [1-Ethyl-5-chloro-4-oxo-2,3,4,9-tetrahydro-1H-(carbazol-1-yl)]-acetic acid 0.4 C$_4$H$_8$O$_2$ The title compound was prepared according to the method of Example 5 using 0.76 g (2.49 mmole) of 1-[ethyl-5-chloro-2,3,4,9-tetrahydro-1H-(carbazol-1-yl)]-acetic acid methyl ester, and was obtained as a white solid, 202°–205° C.

Analysis for: C16 H$_{10}$ ClN O$_3$·0.4 C$_4$H$_8$O$_2$ Calculated: C, 61.99; H, 5.68; N, 4.11. Found: C, 62.19; H, 5.76; N, 3.90. MS: (EI m/z) [M$^+$]305/307

EXAMPLE 13

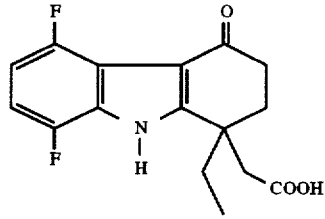

(1-Ethyl-5,8-difluoro-4-oxo-2,3,4,9-tetrahydro-1H-(carbazol-1-yl))-acetic acid

A. (1-Ethyl-5,8-difluoro-2,3,4,9-tetrahydro-1H-(carbazol-1-yl))-acetic acid methyl ester The title compound was prepared according to the method of Example 12, Step A using 20.6 g (0.104 mole) of methyl-1-ethyl-2-oxo-cyclohexane acetate [(Asselin et al *J. Med. Chem.* 19, 787–792 (1976)] and 2,5 difluorophenyl-hydrazine. A crystalline solid (7.35 g, 23%) was obtained having a melting point of 97°–99° C.

Analysis for: $C_{17}H_{19}F_2NO_2$ Calculated: C, 66.44; H, 6.23; N, 4.56 Found: C, 66.15; H, 6.13; N, 4.42

B. (1-Ethyl-5,8-difluoro-4-oxo-2,3,4,9-tetrahydro-1H-(carbazol-1-yl)-acetic acid The title compound was prepared according to the method of Example 5 using 0.200 g (0.622 mmole) of the ester prepared in Step A. The title compound was obtained as a white powder (0.095 g, 50%) having a melting point of 226°–229° C.

Analysis for: $C_{16}H_{15}F_2NO_3$ Calculated: C, 62.54; H, 4.92; N, 4.56 Found: C, 62.78; H, 5.07; N, 4.23

EXAMPLE 14

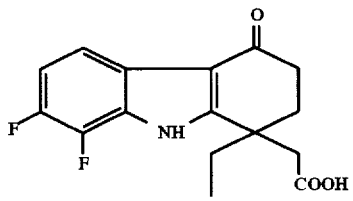

(7,8-Difluoro-1-ethyl-4-oxo-2,3,4,9-tetrahydro-1H-(carbazol-1-yl))-acetic acid

To a stirred solution at room temperature under nitrogen of (7,8-difluoro-1-ethyl-2,3,4,9-tetrahydro-1H-(carbazol-1-yl))acetic acid methyl ester (prepared from 2,3 difluorophenyl hydrazine according to the method of Example 12, Step A, 0.31 g, 1 mmol) in 5 ml of benzene and 5 ml of pH 4 buffer was added dropwise over 1.5 h, a solution of 2,3-dichloro-5,6-dicyano-1,4-benzoquinone (0.522 g, 2.3 mmol) in benzene (30 ml). After 4 h of stirring when the TLC showed ~90% conversion, the mixture was diluted with water (25 ml), ethyl acetate (50 ml), and sodium sulfite (10 ml of a 10% solution). The resulting mixture was stirred for ~10 min (until substantial discoloration occurred), and diluted with 1N NaOH (20 ml). The reaction mixture was extracted with ethyl acetate (50 ml×3). Evaporation of the solvent gave a light brown powder. Purification by flash chromatography (1:1 ethyl acetate:hexane) afforded 0.240 g (72%) of methyl ester which gave after hydrolysis (24 h, MeOH– 1N NaOH), 0.200 g (90%) of the desired product as a white solid, m.p. 259°–261° C.

Analysis for: $C_{16}H_{15}NO_3F_2$ Calculated: C, 62.54; H, 4.92; N, 4.56. Found: C, 62.60; H, 5.16 ; N, 3.90.

$^1$H NMR (400 MHz, DMSO) δ12.30 (s, 1H), 12.20 (s, 1H), 7.18–7.72 (m, 2H), 2.75–3.05 (dd, 2H), 2.2–2.6 (m, 4H), 1.88 (m, 2H).

IR (KBr, cm$^{-1}$): 3240, 2950, 1700, 1660, 1530, 1465

MS (EI m/z): 307, 278, 248.

EXAMPLE 15

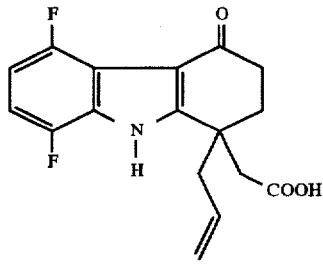

(1-Allyl-5,8-difluoro-4-oxo-2,3,4,9-tetrahydro-1H-(carbazol-1-yl))-acetic acid

A. (1-Allyl-5,8-difluoro-2,3,4,9-tetrahydro-1H-(carhazol-1-yl))-acetic acid methyl ester To a solution of methyl-1-allyl-2-oxo-cyclohexane acetate [prepared analogous to J. Med. Chem. 19, 787 (1976): 19.68 g, 0.094 mole] in toluene (200 ml) was added 2,5-difluorophenylhydrazine (15 g, 0.104 mole). The mixture was refluxed for 24 hours as water was collected in a Dean-Stark trap. The toluene was removed and to the residue was added glacial acetic acid (200 ml) and boron trifluoride diethyl etherate (17.34 g, 0.122 mole). After refluxing for one hour, the mixture was poured into ice (500 ml) and extracted with ether. The combined extracts were washed sequentially with water, 0.5N HCl, 0.5N NaOH and water, dried (MgSO$_4$) and concentrated to a dark oil. The oil was purified by passing through a thick pad of silica gel (eluted with 5–15% ether-hexane) to give 8.58 (28%) orange oil which crystallized upon sitting, m. p. 78°–80° C.

B. (1-Allyl-5,8-difluoro-4-oxo-2,3,4,9-tetrahydro-1H-(carbazol-1-yl))-acetic acid methyl ester A solution of TEMPO$^+$BF$_4^-$ [Bobbitt, J. M., et. al., Heterocycles 30: 1131 (1990); 0.760 g, 3.13 mmole] in 9:1 acetonitrile-water (20 ml) was added dropwise to a solution of the ester prepared according to Step A (0.5 g, 1.56 mmole) in 9:1 acetonitrile-water (20 ml). The reaction was stirred at room temperature for 2.5 hours then the solvent was removed. Water was added to the residue and this extracted with ethyl acetate, dried (MgSO$_4$) and concentrated to a solid. Purification of the solid by flash chromatography (eluted with 95:5 methylene chloride-ethyl acetate) afforded a white solid (0.450 g, 86%), m. p. 179°–181° C.

Analysis for: $C_{18}H_{17}F_2NO_3$ Calculated: C, 64.86; H, 5.14; N, 4.20. Found: C, 64.55; H, 4.98; N, 4.08.

C. (1-Allyl-5,8-difluoro-4-oxo-2,3,4,9-tetrahydro-1H-(carbazol-1-yl))-acetic acid To a solution of the ester prepared in Step B (0.250 g, 0.075 mmole) in tetrahydrofuran (6 ml) was added 1N lithium hydroxide (3 ml) and the mixture was stirred overnight. After removing the solvent, water was added to the residue and this was extracted with methylene chloride. The aqueous layer was acidified (pH 2) and the resulting solid collected, taken into ethyl acetate, dried (MgSO$_4$) and concentrated. The residue was recrystallized (ethyl acetate-hexane) to afford 0.120 g (50%) of white solid, m. p. 205°–206° C.

Analysis for: $C_{17}H_{15}F_2NO_3$ Calculated: C, 63.95; H, 4.74; N, 4.39 Found: C, 63.84; H, 4.57; N, 4.32

EXAMPLE 16

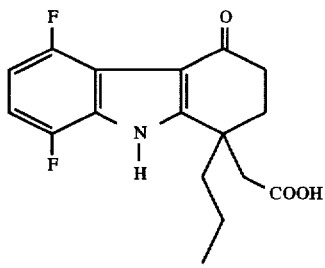

(5,8-Difluoro-4-oxo-1-propyl-2,3,4,9-tetrahydro-1H-(carbazol-1-yl))-acetic acid

A. (5,8-Difluoro-1-propyl-2,3,4,9-tetrahydro-1H-(carbazol-1-yl))-acetic acid methyl ester A mixture of the ester prepared according to Step A of Example 15 (1.0 g, 3.13 mmole) and 10% palladium on carbon (0.050 g) in methanol (30 ml) was shaken on a Parr hydrogenation apparatus starting at 50 psi for 2 h. The catalyst was removed and the filtrate concentrated to yield 0.940 g (94%) of a white solid, m. p. 104°–106° C.

B. (5,8-Difluoro-4-oxo-1-propyl-2,3,4,9-tetrahydro-1H-(carbazol-1-yl))-acetic acid methyl ester The title compound was prepared according to the method of Example 15, Step B using 0.855 g (2.66 mmole) of the ester of Step A, as a white solid (0.690 g, 77%) having a melting point of 205°–207° C.

Analysis for: $C_{18} H_{19} F_2 N O_3$ Calculated: C, 64.47; H, 5.71; N, 4.18. Found: C, 64.38; H, 5.68; N, 4.10.

C. (5,8-Difluoro-4-oxo-1-propyl-2,3,4,9-tetrahydro-1H-(carhazol-1-yl))-acetic acid The title compound was prepared according to the method of Example 15, Step C using 0.550 g (1.64 mmole) of the ester produced in Step B. A white solid (0.271 g, 51%) was obtained having a melting point of 236°–238° C.

Analysis for: $C_{17} H_{17} F_2 N O_3$ Calculated: C, 63.55; H, 5.33; N, 4.36. Found: C, 63.34; H, 5.25; N, 4.28.

EXAMPLE 17

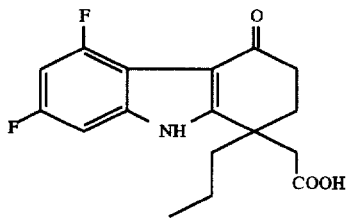

(5,7-Difluoro-1-propyl-4-oxo-2,3,4,9-tetrahydro-1H-(carbazol-1-yl))-acetic acid

A. (5,7-Difluoro-1-propyl-2,3,4,9-tetrahydro-1H-(carbazol-1-yl))-acetic acid methyl ester A mixture of 2,5-difluorophenylhydrazine hydrochloride (10 mmol), 2-propyl-2-(methoxycarbonyl)methylcyclohexanone (Asselin et al *J. Med. Chem* 19, 787–792 (1976), 11 mmol), and sodium acetate (12 mmol) was stirred in methanol (50 ml) for 0.5–4 h at room temperature until reaction was complete (monitored by TLC). The residue after evaporation of the methanol was redissolved in ethyl acetate (100 ml), washed with 1N HCl (50 ml), pH 7 buffer (50 ml), brine, and dried over sodium sulfate. Evaporation of the solvent afforded essentially pure hydrazone. The latter was dissolved in glacial acetic acid (20 ml) and after addition of boron trifluoride etherate (10–12 mmol), quickly heated to reflux. Stirring at reflux was continued until there was complete consumption of hydrazone (usually 20–45 min). After cooling, the mixture was quenched with saturated sodium bicarbonate solution (100 ml) and extracted with ethyl acetate (2×100 ml). The combined organics were washed with brine and dried over sodium sulfate. The crude material that was obtained after evaporation of ethyl acetate was purified by flash chromatography (2–10% EtOAc/hexane) and used as such in the next step.

B. (5,7-Difluoro-1-propyl-4-oxo-2,3,4,9-tetrahydro-1H-(carbazol-1-yl))-acetic acid.

To a stirred solution at room temperature under nitrogen of (5,7-difluoro-1-propyl-2,3,4,9-tetrahydro-1H-carbazol-1-yl)acetic acid methyl ester (0.32 g, 1 mmol) in 5 ml of benzene and 5 ml of pH 4 buffer was added dropwise over 1.5 h, a solution of 2,3-dichloro-5,6-dicyano-1,4-benzoquinone (0.522 g, 2.3 mmol) in benzene (30 ml). After 4 h of stirring when the TLC shows ~90% conversion, the mixture was diluted with water (25 ml), ethyl acetate (50 ml) and 10% sodium sulfite (10 ml). The resulting mixture was stirred for ~10 min (until substantial discoloration occurred) and diluted with 1N NaOH (20 ml). Extraction of the reaction mixture with ethyl acetate (50 ml×3) followed by evaporation of the solvent gave a light brown powder which was purified by flash chromatography (1:1 ethyl acetate:hexane) to afford 0.210 g (63%) of the methyl ester. Hydrolysis (24 h, MeOH ~1N NaOH) gave 0.182 g (90%) of the desired product as a white solid, m.p. 250°–252° C.

Analysis for: $C_{17}H_{17}NO_3F_2$ Calculated: C, 62.54; H, 4.92; N, 4.56. Found: C, 62.15; H, 5.10; N, 4.24.

$^1$H NMR (400 MHz, DMSO) δ12.2 (s, 1H), 12.1 (s, 1H), 6.8–7.1 (m, 2H), 2.6–2.9 (dd, 2H), 2.0–2.3 (m, 2H), 0.84 (t, 3H).

IR (KBr, $cm^{-1}$): 3250, 2950, 1700, 1630, 1450
MS [(−)FAB m/z]: 320

EXAMPLE 18

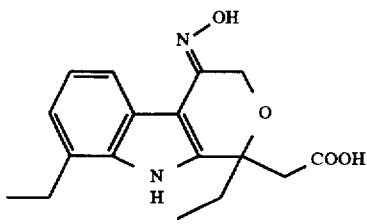

[1,8-Diethyl-4-hydroxyimino-1,3,4,9-tetrahydropyrano [3,4-b] indol-1-yl]- acetic acid A. [1,8-Diethyl-4-hydroxyimino-1,3,4,9-tetrahydro-pyrano [3,4-b] indol-1-yl]- acetic acid methyl ester The ester of Example 4, Step B (0.5 g, 1.6 mmol), hydroxylamine hydrochloride (0.17 g, 2.4 mmol), and 25 ml pyridine were refluxed for 3.5 h. The reaction mixture was poured into water, extracted with $CHCl_3$. The organic phase was then washed with 1.0N HCl, water, dilute $NaHCO_3$, water, and brine, dried ($MgSO_4$) and evaporated to yield a crude solid which was purified by filtration through a pad of silica gel and celite. The product, 0.33 g was isolated as a solid, m. p. 188°–190° C.

Analysis for: $C_{18} H_{22} N_2 O_4$ Calculated: C, 65.44; H, 6.71; N, 8.48. Found: C, 65.59; H, 6.80; N, 8.27

B. [1,8-Diethyl-4-hydroxyimino-1,3,4,9-tetrahydro-pyrano [3,4-b] indol-1-yl]- acetic acid 0.06 ethyl acetate.

The product of Step A (0.182 g, 0.55 mmol), K₂CO₃ (0.1 g, 0.71 mmol) and a MeOH—H₂O mixture (10 ml-1 ml) were refluxed for 3 h. The reaction mixture was cooled to room temperature and the methanol was removed. To the reaction mixture was added 10 ml H₂O, which was then acidified using 1N HCl. The aqueous phase was extracted with EtOAc, which was dried (MgSO₄), evaporated and triturated using hexane to yield a solid, m.p. 165°–168° C. (dec.).

Analysis for: $C_{17} H_{20} N_2 O_4 \cdot 0.06$ EtOAc Calculated: C, 64.38; H, 6.41; N, 8.71. Found: C, 64.08; H 6.48; N, 8.21.

EXAMPLE 19

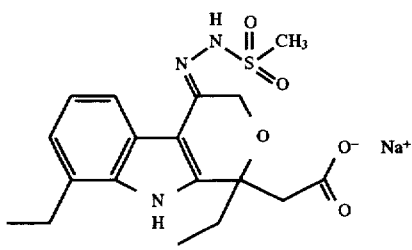

[1,8-Diethyl-4-(methanesulfonyl-hydrazono)-1,3,4,9-tetrahydro-pyrano [3,4-b] indol-1-yl]-acetic acid sodium salt A. [1,8-Diethyl-4-(methanesulfonyl-hydrazono)-1,3,4,9-tetrahydro-pyrano [3,4-b] indol-1-yl]-acetic acid methyl ester To the ester of Example 4, Step B (0.5 g, 1.6 mmol) was added 10 ml MeOH, 0.4 ml 1N HCl and 0.37 ml H₂O. The mixture was stirred one minute followed by addition of CH₃SO₂NHNH₂ all at once. After overnight stirring, the MeOH was evaporated and additional water was added. This aqueous phase was twice extracted with CH₂Cl₂. The organic phase was concentrated to a crude solid and purified by flash chromatography using CH₂Cl₂—EtOAc 95-5 as eluent. The product 0.33 g, was obtained as a solid m.p. 80°–82° C.

MS (EI, m/z): 407 (M)⁺.

B. [1,8-Diethyl-4-(methanesulfonyl-hydrazono)-1,3,4,9-tetrahydro-pyrano [3,4-b] indol-1-yl]-acetic acid sodium salt The title compound was prepared according to the method of Example 18, Step B using 0.2 g (0.49 mmol) of the ester from Step A. Trituration in ethyl ether gave the product 0.12 g, as a solid, m.p. 187°–190° C.

MS [(−)FAB m/z]: 392 (M)⁺.

EXAMPLE 20

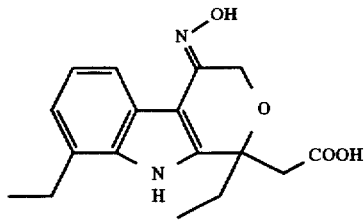

(1,8-Diethyl-4-hydroxyimino-2,3,4,9-tetrahydro-1H-carbazol-1-yl)-acetic acid

The title compound was prepared according to the method of Example 18, using of the ester from Example 10. The title compound was obtained as a white solid, m.p. 203°–206° C.

Analysis for: $C_{18} H_{22} N_2 O_3$ Calculated: C, 68.77; H, 7.05; N, 8.91. Found: C, 68.40; H 7.11; N, 8.82.

What is claimed is:

1. A compound of formula I having the structure

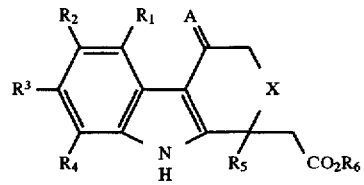

wherein

R₁, R₂, R₃ and R₄ are, each, independently, hydrogen, alkyl of 1–6 carbon atoms, alkenyl of 2–7 carbon atoms, alkynyl of 2–7 carbon atoms, alkoxy of 1–6 carbon atoms, aralkoxy of 7 to 12 carbon atoms, trifluoroalkoxy, alkanoyloxy of 2–6 carbon atoms, hydroxy, halo, trifluoromethyl, cyano, amino, mono- or di-alkylamino in which each alkyl group has 1–6 carbon atoms, alkanamido of 2–6 carbon atoms, or alkanesulfonamido of 1–6 carbon atoms;

R₅ is hydrogen, alkyl of 1–6 carbon atoms, alkenyl of 2–7 carbon atoms, alkoxyalkyl in which each alkyl moiety has 1–6 carbon atoms or alkylcycloalkyl in which the alkyl moiety has 1–6 carbon atoms and the cycloalkyl moiety has 3–8 carbon atoms;

R₆ is hydrogen, alkyl of 1–6 carbon atoms or alkenyl of 2–7 carbon atoms;

X is oxygen;

A is NZ;

Z is hydroxyl, alkoxy, aryloxy, carboxyalkyloxy of 2–7 carbon atoms, arylamino, or alkylsulfonyamino of 1–6 carbon atoms;

or a pharmaceutically acceptable salt thereof.

2. The compound according to claim 1, wherein R₆ is hydrogen or a pharmaceutically acceptable salt thereof.

3. The compound according to claim 2, wherein R₅ is alkyl of 1–6 carbon atoms, alkenyl of 1–6 carbon atoms, or alkoxyalkyl in which each alkyl moiety has 1–6 carbon atoms or a pharmaceutically acceptable salt thereof.

4. The compound according to claim 1, which is [1,8-diethyl-4-hydroxyimino-1,3,4,9-tetrahydro-pyrano[3,4-b] indol-1-yl]-acetic acid or a pharmaceutically acceptable salt thereof.

5. The compound according to claim 1, which is [1,8-diethyl-4-(methanesulfonyl-hydrazono)-1,3,4,9-tetrahydro-pyrano[3,4-b]indol-1-yl]-acetic acid sodium salt.

6. A method of treating arthritic disorders in a mammal in need thereof which comprises administering to said mammal an effective amount of a compound of formula I having the structure

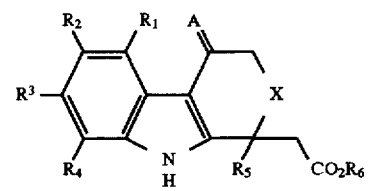

wherein

R₁, R₂, R₃ and R₄ are, each, independently, hydrogen, alkyl of 1–6 carbon atoms, alkenyl of 2–7 carbon atoms, alkynyl of 2–7 carbon atoms, alkoxy of 1–6 carbon atoms, aralkoxy of 7 to 12 carbon atoms, trifluroalkoxy, alkanoyloxy of 2–6 carbon atoms, hydroxy, halo, trifluoromethyl, cyano, amino, mono- or di-alkylamino in which each alkyl group has 1–6 carbon atoms, alkanamido of 2–6 carbon atoms, or alkanesulfonamido of 1–6 carbon atoms;

$R_5$ is hydrogen, alkyl of 1–6 carbon atoms, alkenyl of 2–7 carbon atoms, alkoxyalkyl in which each alkyl moiety has 1–6 carbon atoms or alkylcycloalkyl in which the alkyl moiety has 1–6 carbon atoms and the cycloalkyl moiety has 3–8 carbon atoms;

$R_6$ is hydrogen, alkyl of 1–6 carbon atoms or alkenyl of 2–7 carbon atoms;

X is oxygen;

A is NZ;

Z is hydroxyl, alkoxy, aryloxy, carboxyalkyloxy of 2–7 carbon atoms, arylamino, or alkylsulfonyamino of 1–6 carbon atoms;

or a pharmaceutically acceptable salt thereof.

7. A method of treating colorectal cancer in a mammal in need thereof which comprises administering to said mammal an effective amount of a compound of formula I having the structure

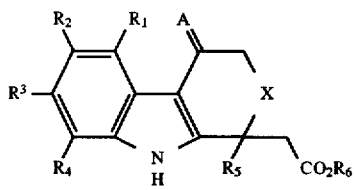

wherein $R_1$, $R_2$, $R_3$ and $R_4$ are, each, independently, hydrogen, alkyl of 1–6 carbon atoms, alkenyl of 2–7 carbon atoms, alkynyl of 2–7 carbon atoms, alkoxy of 1–6 carbon atoms, aralkoxy of 7 to 12 carbon atoms, trifluroalkoxy, alkanoyloxy of 2–6 carbon atoms, hydroxy, halo, trifluoromethyl, cyano, amino, mono- or di-alkylamino in which each alkyl group has 1–6 carbon atoms, alkanamido of 2–6 carbon atoms, or alkanesulfonamido of 1–6 carbon atoms;

$R_5$ is hydrogen, alkyl of 1–6 carbon atoms, alkenyl of 2–7 carbon atoms, alkoxyalkyl in which each alkyl moiety has 1–6 carbon atoms or alkylcycloalkyl in which the alkyl moiety has 1–6 carbon atoms and the cycloalkyl moiety has 3–8 carbon atoms;

$R_6$ is hydrogen, alkyl of 1–6 carbon atoms or alkenyl of 2–7 carbon atoms;

X is oxygen;

A is oxygen or NZ;

Z is hydroxyl, alkoxy, aryloxy, carboxyalkyloxy of 2–7 carbon atoms, arylamino, or alkylsulfonyamino of 1–6 carbon atoms;

or a pharmaceutically acceptable salt thereof.

8. A method of treating Alzheimer's disease in a mammal which comprises administering to said person an effective amount of a compound of formula I having the structure

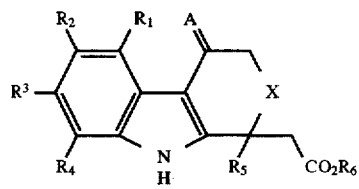

wherein $R_1$, $R_2$, $R_3$ and $R_4$ are, each, independently, hydrogen, alkyl of 1–6 carbon atoms, alkenyl of 2–7 carbon atoms, alkynyl of 2–7 carbon atoms, alkoxy of 1–6 carbon atoms, aralkoxy of 7 to 12 carbon atoms, trifluroalkoxy, alkanoyloxy of 2–6 carbon atoms, hydroxy, halo, trifluoromethyl, cyano, amino, mono- or di-alkylamino in which each alkyl group has 1–6 carbon atoms, alkanamido of 2–6 carbon atoms, or alkanesulfonamido of 1–6 carbon atoms;

$R_5$ is hydrogen, alkyl of 1–6 carbon atoms, alkenyl of 2–7 carbon atoms, alkoxyalkyl in which each alkyl moiety has 1–6 carbon atoms or alkylcycloalkyl in which the alkyl moiety has 1–6 carbon atoms and the cycloalkyl moiety has 3–8 carbon atoms;

$R_6$ is hydrogen, alkyl of 1–6 carbon atoms or alkenyl of 2–7 carbon atoms;

X is oxygen;

A is oxygen or NZ;

Z is hydroxyl, alkoxy, aryloxy, carboxyalkyloxy of 2–7 carbon atoms, arylamino, or alkylsulfonyamino of 1–6 carbon atoms;

or a pharmaceutically acceptable salt thereof.

9. A pharmaceutical composition which comprises a compound of formula I having the structure

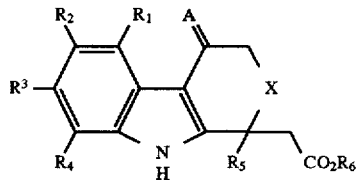

wherein $R_1$, $R_2$, $R_3$ and $R_4$ are, each, independently, hydrogen, alkyl of 1–6 carbon atoms, alkenyl of 2–7 carbon atoms, alkynyl of 2–7 carbon atoms, alkoxy of 1–6 carbon atoms, aralkoxy of 7 to 12 carbon atoms, trifluroalkoxy, alkanoyloxy of 2–6 carbon atoms, hydroxy, halo, trifluoromethyl, cyano, amino, mono- or di-alkylamino in which each alkyl group has 1–6 carbon atoms, alkanamido of 2–6 carbon atoms, or alkanesulfonamido of 1–6 carbon atoms;

$R_5$ is hydrogen, alkyl of 1–6 carbon atoms, alkenyl of 2–7 carbon atoms, alkoxyalkyl in which each alkyl moiety has 1–6 carbon atoms or alkylcycloalkyl in which the alkyl moiety has 1–6 carbon atoms and the cycloalkyl moiety has 3–8 carbon atoms;

$R_6$ is hydrogen, alkyl of 1–6 carbon atoms or alkenyl of 2–7 carbon atoms;

X is oxygen;

A is NZ;

Z is hydroxyl, alkoxy, aryloxy, carboxyalkyloxy of 2–7 carbon atoms, arylamino, or alkylsulfonyamino of 1–6 carbon atoms;

or a pharmaceutically acceptable salt thereof and a pharmaceutical carrier.

10. A process for the preparation of a compound of formula I having the structure

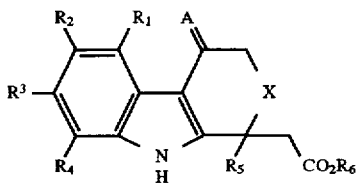

wherein $R_1$, $R_2$, $R_3$ and $R_4$ are, each, independently, hydrogen, alkyl of 1–6 carbon atoms, alkenyl of 2–7 carbon atoms, alkynyl of 2–7 carbon atoms, alkoxy of 1–6 carbon atoms, aralkoxy of 7 to 12 carbon atoms, trifluroalkoxy, alkanoyloxy of 2–6 carbon atoms, hydroxy, halo, trifluoromethyl, cyano, amino, mono- or di-alkylamino in which each alkyl group has 1–6 carbon atoms, alkanamido of 2–6 carbon atoms, or alkanesulfonamido of 1–6 carbon atoms;

$R_5$ is hydrogen, alkyl of 1–6 carbon atoms, alkenyl of 2–7 carbon atoms, alkoxyalkyl in which each alkyl moiety has 1–6 carbon atoms or alkylcycloalkyl in which the alkyl moiety has 1–6 carbon atoms and the cycloalkyl moiety has 3–8 carbon atoms;

$R_6$ is hydrogen, alkyl of 1–6 carbon atoms or alkenyl of 2–7 carbon atoms;

X is oxygen;

A is NZ;

Z is hydroxyl, alkoxy, aryloxy, carboxyalkyloxy of 2–7 carbon atoms, arylamino, or alkylsulfonyamino of 1–6 carbon atoms;

or a pharmaceutically acceptable salt thereof, which comprises (a) reacting of a compound having the formula I where A is oxygen and $R_1$, $R_2$, $R_3$, $R_4$, $R_5$, $R_6$ and X are as defined above or a salt thereof with a compound having the formula $H_2NZ$ where Z is as defined above to prepare a compound having formula I as illustrated above where A is NZ and $R_1$, $R_2$, $R_3$, $R_4$, $R_5$, $R_6$, and X are as defined above or a salt thereof; or (b) hydrolyzing a compound having formula I as illustrated above where A, $R_1$, $R_2$, $R_3$, $R_4$, $R_5$ and X are as defined above and $R_6$ is alkyl of 1–6 carbon atoms or alkenyl of 2–7 carbon atoms so as to form a compound having formula I as illustrated above where A, $R_1$, $R_2$, $R_3$, $R_4$, $R_5$, $R_6$ and X are as defined above and $R_6$ is hydrogen or a salt thereof.

* * * * *

UNITED STATES PATENT AND TRADEMARK OFFICE
CERTIFICATE OF CORRECTION

PATENT NO.    : 5,776,967

DATED         : July 7, 1998

INVENTORS     : Anthony F. Kreft, Craig E. Caufield, Amedeo A. Failli, Thomas J. Caggiano, Alexander A. Greenfield, Dennis M. Kubrak It is certified that errors appear in the above-identified patent and that said Letters Patent are hereby corrected as shown below:

On the title page,
    column 1, below the filing date of the application, insert:

-- Related U.S. Application Data
Provisional application No. 60/022,471 Jul. 26, 1996.    --

Signed and Sealed this

Fifteenth Day of June, 1999

*Attest:*

Q. TODD DICKINSON

*Attesting Officer*      *Acting Commissioner of Patents and Trademarks*